United States Patent
Luo

(10) Patent No.: US 9,306,425 B2
(45) Date of Patent: Apr. 5, 2016

(54) SPRING MOTOR

(76) Inventor: Ming Luo, Shenzhen (CN)

( * ) Notice: Subject to any disclaimer, the term of this patent is extended or adjusted under 35 U.S.C. 154(b) by 101 days.

(21) Appl. No.: 13/980,829

(22) PCT Filed: Jan. 16, 2012

(86) PCT No.: PCT/CN2012/000066
§ 371 (c)(1),
(2), (4) Date: Sep. 6, 2013

(87) PCT Pub. No.: WO2012/097677
PCT Pub. Date: Jul. 26, 2012

(65) Prior Publication Data
US 2013/0334905 A1    Dec. 19, 2013

(30) Foreign Application Priority Data
Jan. 19, 2011  (CN) .......................... 2011 1 0022248

(51) Int. Cl.
*H02K 3/51* (2006.01)
*A61C 17/34* (2006.01)
*H02K 33/00* (2006.01)
*H02K 33/02* (2006.01)
*H02K 7/14* (2006.01)

(52) U.S. Cl.
CPC .............. *H02K 3/51* (2013.01); *A61C 17/3418* (2013.01); *H02K 33/00* (2013.01); *H02K 33/02* (2013.01); *H02K 7/14* (2013.01)

(58) Field of Classification Search
CPC ....... H02K 33/16; H02K 33/00; H02K 33/04; H02K 3/51; H02K 7/142; A61C 17/3418
See application file for complete search history.

(56) References Cited

U.S. PATENT DOCUMENTS

| | | | | |
|---|---|---|---|---|
| 3,598,932 | A * | 8/1971 | Gaudry et al. | 191/12.2 R |
| 4,494,024 | A * | 1/1985 | Braun | 310/75 A |
| 6,664,668 | B2 * | 12/2003 | Furuya et al. | 310/216.004 |
| 7,569,958 | B2 * | 8/2009 | Matsuzaki et al. | 310/71 |
| 7,960,877 | B2 * | 6/2011 | Luo | 310/38 |
| 2004/0026178 | A1 * | 2/2004 | Honda | 187/251 |
| 2006/0138892 | A1 * | 6/2006 | Hagino et al. | 310/198 |
| 2012/0074795 | A1 * | 3/2012 | Nishikawa et al. | 310/23 |

* cited by examiner

Primary Examiner — Michael Zarroli

(57) ABSTRACT

A spring motor, comprising a housing, a stator core, a rotor core, a rotation shaft, a rotor coil, an insulated coil connection wire, a torsion spring, a connection shaft, a cylindrical spiral spring, a round funnel-shaped rubber sealing element, a battery and a spring fixing connection sleeve; the rotor coil of the motor is connected to the terminal of a motor end cover after the insulated coil connection wire winds around the periphery of the rotation shaft continuously several times; the connection shaft is fixed on the rotation shaft, and the cylindrical spiral spring is sleeved on the periphery of the opened end of the connection shaft; the round funnel-shaped waterproof rubber sealing element is sleeved on the rotation shaft; the battery is placed in a rectangular battery holder, three side frames of the battery holder are each a fixed structure, and one side frame of the battery holder is a moveable structure; the spring fixing connection sleeve is sleeved on the rotation shaft, the rear end of the torsion spring is placed on one side of the spring fixing connection sleeve, and the spring fixing connection jacket, the torsion spring and the rotation shaft are fixed and connected with screws.

7 Claims, 1 Drawing Sheet

U.S. Patent　　　　　　　　　　Apr. 5, 2016　　　　　　　　　US 9,306,425 B2
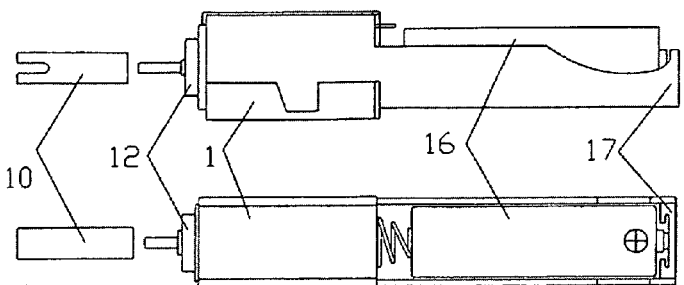
FIGURE 1
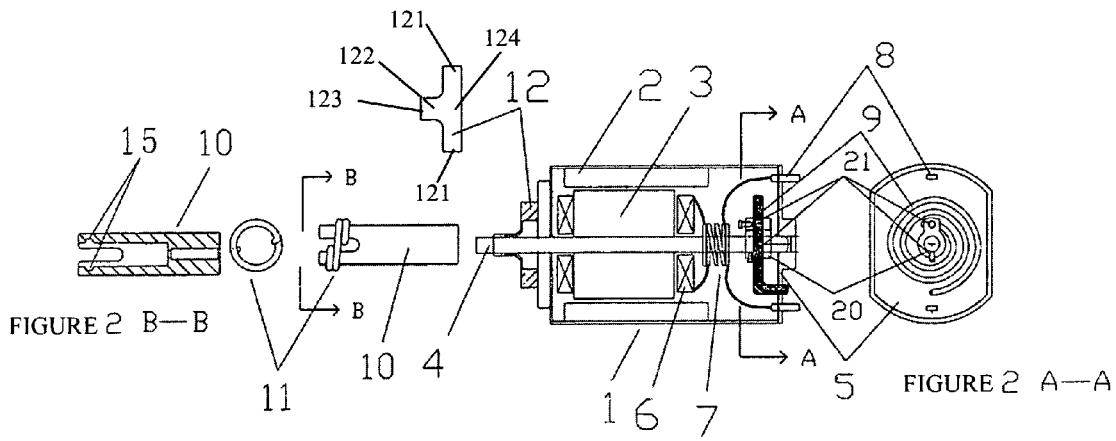
FIGURE 2 B—B　　　　　　　　　　　　　　　　　　FIGURE 2 A—A
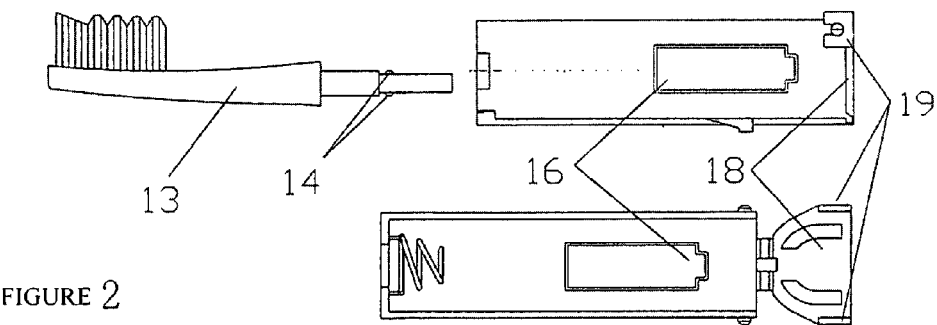
FIGURE 2
FIGURE 3
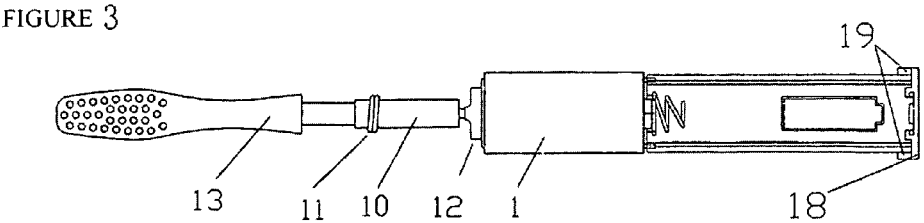

SPRING MOTOR

BACKGROUND OF THE PRESENT INVENTION

1. Field of Invention

The present invention relates to motor and application, in particular to a reciprocating oscillation brushless pulse motor (also known as reciprocating motor or spring motor)and problems of connecting and used of electric reciprocating motion device.

2. Description of Related Arts

The existing reciprocating oscillation spring motor and electric reciprocating motion device (disclosed in Chinese patent CN2498787Y "RECIPROCATING OSCILLATING BRUSHLESS PULSE MOTOR", ZL2006200158088 "ELECTRIC RECIPROCATING MOTION DEVICE" and ZL200920261847X "SPRING MOTOR") have some disadvantages in connection and application. Firstly, the connecting wire of the inner rotor coil of the spring motor is easily bending fatigue and broken due to the continuous reciprocating oscillation of the rotation shaft during the operation of motor and then the motor is power off and can not work. Secondly, because there is no elastic device provided at the opening end of the connecting shaft, the moving head is easily detached during fixing or operation, and then cause potential safety hazards. Thirdly, the sealing ring sleeved on the motor shaft is a round flat rubber element, and this kind of sealing ring can provide large resistance to the rotation shaft. Fourthly, the existing battery holder is a rectangle structure closed by four edges. The disadvantage of this structure is the shell must has larger capacity, otherwise the battery is difficult to be placed or taken out. Fifthly, the fixing of one end of the spring is inconvenient.

SUMMARY OF THE PRESENT INVENTION

The technical problem to be solved by the present invention is providing a connection method and design of simple structure and easy assembling. The spring motor and devices can be used more easily, safely and reliably.

The technical problems of the present invention are solved in the following manner. In terms of the first problem described in the background, the connecting wire of the rotor coil is connected to the terminal of the motor end cover or lead out of the motor through the end cover after winding several times on the rotation shaft, but not directly connected to the terminal of the motor end cover.

In terms of the second problem described in the background, a cylindrical helical spring is sleeved on the opening end of the connecting shaft, and the connecting force between the moving head and connecting shaft can be adjusted by changing the size, material, shape of the spring 11 and the relative position between spring and connection shaft, so as to realize a convenient and reliable connection.

In terms of the third problem described in the background, the existing sealing ring of round flat rubber element is replaced by a round funnel-shaped rubber element.

In terms of the fourth problem described in the background, the rectangular structure closed by four edges is changed to a structure with three fixed edges and one movable edge, and then the battery is conveniently to be placed or taken out.

In terms of the fifth problem described in the background, the existing spring seat and the connection method that spring is fixed on the rotation shaft are replaced by providing a spring fixing connecting sleeve, and then it is convenient to fix or replace the spring.

Compared with the motor of the prior art, the connection and structure of the spring motor of present invention have advantages of simple structure, easy use and reliable operation.

According to the present invention, the foregoing and other objects and advantages are attained by a spring motor which comprises: a stator core, a rotor core, a rotation shaft, an end cover, a rotor coil, a coil connecting wire, a wiring terminal and a battery. In one embodiment, the rotor coil is connected to the wiring terminal of the end cover after the connecting wire winding several turns on the rotation shaft, thus the breaking of the wire for bending fatigue due to the continuous reciprocating movement during the operation of the motor can be avoided, and the rotor coil is directly lead out of the spring motor through the end cover.

In another embodiment, a cylindrical connecting shaft is fixed on the rotation shaft, and a cylindrical helical spring is sleeved on the opening end of the connecting shaft, a moving head is inserted into the connection shaft from the opening end thereof, the position of the convex point on the outside surface of the moving head is corresponding to that of the concavity arranged in the inner side of the opening end of the connection shaft, thus the relative movement between the moving head and connecting shaft can be avoided, the connecting force between the moving head and the connecting shaft can be adjusted by changing the size, material, shape of the spring and the relative position between spring and the connection shaft, so as to realize a convenient and reliable connection.

In still another embodiment, a round funnel-shaped sealing rubber element is sleeved on the rotation shaft, the two ends of the round funnel-shaped sealing rubber element are thicker than the middle part, the small end of the rubber element is sleeved on the connecting shaft tightly, while the large end is pressed on the front end of the motor shell, so as to prevent water from entering into the motor through the connecting shaft, because the material of the middle part of the rubber element is thin and elastic, when the motor is reciprocal winging, the resistance produced by the rubber element is very small, thus the resistance and energy consumption during the operation of the motor rotation shaft are reduced, and the life of the sealing ring is prolonged.

In a further embodiment, a battery holder has three fixed edges and one movable edge, and the movable edge can be opened or closed by a movable fastener positioned on two sides of the movable edge.

In still a further embodiment, a spring fixing connecting sleeve is sleeved on the rotation shaft, the end of a torsion spring is placed on one side of the sleeve, the spring fixing connecting sleeve and the torsion spring can be conveniently fixed and connected to each other by a screw, the spring fixing connecting sleeve and the torsion spring can be fixed relatively on inside or outside of the motor.

BRIEF DESCRIPTION OF THE DRAWINGS

FIG. 1 shows part of "electric reciprocating motion device" of existing patent.

FIG. 2 shows the connection of the inside and outside of the spring motor according to the present invention.

FIG. 3 shows the whole structure of the spring motor of present invention.

DETAILED DESCRIPTION OF THE PREFERRED EMBODIMENT

As shown in FIGS. 1 and 2, it's structure comprises rotor and shell 1, stator core 2, rotor core 3, rotation shaft 4, end cover 5, rotor coil 6, coil connecting wire 7, wiring terminal 8, torsion spring 9, connecting shaft 10, concavity 15 arranged in the inner side of the opening end, cylindrical helical spring 11, round funnel-shaped sealing rubber element 12, moving head 13, positioning convex point 14, battery 16, traditional battery holder 17, battery holder 18 of present invention, movable fastener 19, spring fixing connecting sleeve 20 and fixing screw 21. As shown in FIG. 2, the connecting wire 7 of the rotor coil 6 is connected to the terminal 8 of the motor end cover 5 (or lead out of the motor through the end cover)after winding several times on the rotation shaft 4. The breaking of the wire for bending fatigue due to the continuous reciprocating movement during the operation of the motor can be avoided by the said method, if only appropriate diameter and number of turns of the connecting wire are selected.

Furthermore, as shown in FIGS. 1 and 2, the cylindrical connecting shaft 10 is fixed on the rotation shaft 4 of the motor. A cylindrical helical spring 11 is sleeved on the opening end of the connecting shaft 10. The moving head 13 is inserted into the connection shaft 10 from the opening end thereof. The position of the convex point 14 on the outside surface of the moving head 13 is corresponding to that of the concavity 15 arranged in the inner side of the opening end of the connection shaft 10, thus the relative movement between the moving head 13 and connecting shaft 10 can be avoided. The connecting force between the moving head 13 and connecting shaft 10 can be adjusted by changing the size, material, shape of the spring 11 and the relative position between spring 11 and connection shaft 10, so as to realize a convenient and reliable connection.

Furthermore, as shown in FIG. 2, a round funnel-shaped sealing rubber element 12 is sleeved on the rotation shaft 4. The two ends 121 of the sealing ring 12 are thicker than the middle part 122. The small end 123 of the sealing ring 12 is sleeved on the motor shaft 4 tightly, while the large end 124 is pressed on the front end of the motor shell 1, so as to prevent water from entering into the motor. Because the material of the middle part 122 of the sealing ring 12 is thin and elastic, when the motor is reciprocal winging, the resistance produced by the sealing ring 12 is very small, thus the resistance and energy consumption during the operation of the motor rotation shaft 4 are reduced, and the life of the sealing ring 12 is prolonged.

Furthermore, as shown in FIG. 1, the battery 16 is placed in a rectangular battery holder 17 closed by four edges. The battery 16 must be placed or taken out in the direction of vertical, and this will be inconvenient if the inner capacity of the products is not enough. As shown in FIG. 2, the rectangular structure closed by four edges is changed to a structure with three fixed edges and one movable edge 18, and then the battery is conveniently to be placed or taken out. The edge 18 can be opened or closed by fasteners 19 positioned on two sides of the edge. This design also can be used in the battery holder of other similar electronic products.

Finally, as shown in FIGS. 2 and 2A-A, a spring fixing connecting sleeve 20 is provided and sleeved on the rotation shaft 4. End of the spring 9 is placed on one side of the sleeve 20. The spring fixing connecting sleeve 20, spring 9 and rotation shaft 4 can be fixed and connected to each other by screw 21. The spring fixing connecting sleeve 20 and spring 9 can be fixed relatively on inside or outside of the motor.

What is claimed is:

1. A spring motor, comprising: a stator core, a rotor core, a rotation shaft, an end cover comprising a wiring terminal, a rotor coil comprising a coil connecting wire and a battery, wherein the rotor coil is connected to the wiring terminal of the end cover after the connecting wire is wound several turns on the rotation shaft such that the bending fatigue of the connecting wire is reduced during the operation of the motor, wherein a cylindrical connecting shaft is fixed on the rotation shaft, and a cylindrical helical spring is sleeved on an opening end of the connecting shaft, a moving head is inserted into the connection shaft from the opening end thereof, wherein a convex point on an outside surface of the moving head is corresponding to a concavity arranged in an inner side of the opening end of the connection shaft such that the relative movement between the moving head and the connecting shaft is avoided, the connecting force between the moving head and the connecting shaft is allowed to be adjusted by changing the size, material, shape of the cylindrical helical spring and the relative position between the cylindrical helical spring and the connection shaft.

2. A spring motor, comprising: a stator core, a rotor core, a rotation shaft, an end cover comprising a wiring terminal, a rotor coil comprising a coil connecting wire and a battery, wherein the rotor coil is connected to the wiring terminal of the end cover after the connecting wire is wound several turns on the rotation shaft such that the bending fatigue of the connecting wire is reduced during the operation of the motor, wherein a round funnel-shaped sealing rubber element is sleeved on the rotation shaft, wherein the round funnel-shaped sealing rubber element has two ends, a middle part, a small end and a large end, wherein the ends of the round funnel-shaped sealing rubber element are thicker than the middle part thereof, the small end of the round funnel-shaped sealing rubber element is sleeved on the connecting shaft tightly, and the large end is pressed on the front end of the motor shell, so as to prevent water from entering into the motor through the connecting shaft, wherein the material of the middle part of the round funnel-shaped sealing rubber element is thin and elastic such that when the motor swings in a reciprocating manner, the resistance is produced by the round funnel-shaped sealing rubber element and the resistance and energy consumption thereof are reduced, during the operation of the motor rotation shaft.

3. The spring motor, as recited in claim 1, wherein a round funnel-shaped sealing rubber element is sleeved on the rotation shaft, wherein the round funnel-shaped sealing rubber element has two ends, a middle part, a small end and a large end, wherein the ends of the round funnel-shaped sealing rubber element are thicker than the middle part thereof, the small end of the round funnel-shaped sealing rubber element is sleeved on the connecting shaft tightly, and the large end is pressed on the front end of the motor shell, so as to prevent water from entering into the motor through the connecting shaft, wherein the material of the middle part of the round funnel-shaped sealing rubber element is thin and elastic, such that when the motor swings in a reciprocating manner, the resistance is produced by the round funnel-shaped sealing rubber element and the resistance and energy consumption thereof are reduced, during the operation of the motor rotation shaft.

4. The spring motor, as recited in claim 1, further comprising a spring fixing connecting sleeve is sleeved on the rotation shaft, wherein an end of a torsion spring is placed on one side of the spring fixing connecting sleeve, wherein the spring fixing connecting sleeve and the torsion spring are conveniently fixed and connected to each other by a screw, wherein the spring fixing connecting sleeve and the torsion spring are fixed on the inside or the outside of the motor.

5. The spring motor, as recited in claim 2, further comprising a spring fixing connecting sleeve is sleeved on the rotation shaft, wherein an end of a torsion spring is placed on one side of the spring fixing connecting sleeve, wherein the spring fixing connecting sleeve and the torsion spring are conveniently fixed and connected to each other by a screw, wherein the spring fixing connecting sleeve and the torsion spring are fixed on the inside or the outside of the motor.

6. The spring motor, as recited in claim 3, further comprising a spring fixing connecting sleeve is sleeved on the rotation shaft, wherein an end of a torsion spring is placed on one side of the spring fixing connecting sleeve, wherein the spring fixing connecting sleeve and the torsion spring are conveniently fixed and connected to each other by a screw, wherein the spring fixing connecting sleeve and the torsion spring are fixed on the inside or the outside of the motor.

7. A spring motor, comprising: a stator core, a rotor core, a rotation shaft, an end cover comprising a wiring terminal, a rotor coil comprising a coil connecting wire and a battery, a spring fixing connecting sleeve sleeved on the rotation shaft, wherein the rotor coil is connected to the wiring terminal of the end cover after the connecting wire is wound several turns on the rotation shaft such that the bending fatigue of the connecting wire is reduced during the operation of the motor, wherein an end of a torsion spring is placed on one side of the spring fixing connecting sleeve, wherein the spring fixing connecting sleeve and the torsion spring are conveniently fixed and connected to each other by a screw, wherein the spring fixing connecting sleeve and the torsion spring are fixed on the inside or the outside of the motor.

\* \* \* \* \*